US006982152B2

(12) United States Patent
Riss et al.

(10) Patent No.: US 6,982,152 B2
(45) Date of Patent: Jan. 3, 2006

(54) CYTOTOXICITY ASSAY

(75) Inventors: Terry L. Riss, Oregon, WI (US); Richard A. Moravec, Oregon, WI (US)

(73) Assignee: Promega Corporation, Madison, WI (US)

(*) Notice: Subject to any disclaimer, the term of this patent is extended or adjusted under 35 U.S.C. 154(b) by 535 days.

(21) Appl. No.: 10/124,029

(22) Filed: Apr. 17, 2002

(65) Prior Publication Data

US 2003/0203420 A1 Oct. 30, 2003

(51) Int. Cl.
*C12Q 1/18* (2006.01)

(52) U.S. Cl. .......................................... 435/32; 435/25
(58) Field of Classification Search .................. 435/32, 435/4, 25, 26, 29, 34, 190; 424/9.2
See application file for complete search history.

(56) References Cited

U.S. PATENT DOCUMENTS

| | | | |
|---|---|---|---|
| 3,107,204 | A | 10/1963 | Brown et al. |
| 4,849,347 | A | 7/1989 | Familletti et al. |
| 5,185,450 | A | 2/1993 | Owen |
| 5,501,959 | A | 3/1996 | Lancaster et al. |
| 5,756,527 | A | 5/1998 | Mjalli et al. |
| 5,858,974 | A | 1/1999 | Little, II et al. |
| 5,912,139 | A | 6/1999 | Iwata et al. |
| 6,811,990 | B1 | 11/2004 | Corey et al. |

FOREIGN PATENT DOCUMENTS

| | | |
|---|---|---|
| CA | 1112140 | 11/1981 |
| JP | 2211 899 | 4/1990 |
| WO | WO 01/98531 A1 | 12/2001 |

OTHER PUBLICATIONS

Dunigan D. Aqueous Soluble Tetrazolium/Formazan MTS as an Indicator of NADH and NADPH Dependent Dehydrogenase Activity. BioTechniques 19(4)640–649, 1995.*
O'Brien J. Investigation of the Alamar Blue (Resazurin) Fluoresecent Dye for the Assessment of Mammalian Cell Cytotoxicity. Eur J Biochem 267(1)5421–6, 2000.*
Amaksu et al., (1986), *Tohoku J. Exp. Med.* 149:343–350.
Buttke et al., (1993)*J. Immunol. Methods* 157:233–240.
Corey et al.,(1997)*J. Immunol. Meth.* 207:43–51.
Dunigan et al., (1995), *BioTechniques* 19:640–649.
Evans et al., (2001) *Toxicology in Vitro*15:579–584.
Horobin, RW, (2001) *Biotechnic & Histochemistry*76(4):163–164.
Kanazawa et al., (1966) *J. Antibiotics*19:229–233.
Liu, D. (1981) *Bull. Environ. Contam. Toxicol.*26:145–149.
Miura et al., (1987) *Analytical Biochemistry*164:482–487.
Shahangian et al., (1984) *Journal of Analytical Toxicology*, vol. 8, pp. 273–276.
Soyama et al., (1987) *Clinica Chimica Acta,*168:259–260.
Winartasputra et al., (1980) *Clin. Chem.*26/5:613–617.
Evans et al., (2001) *Toxicology in Vitro* 15:579–584.
Horobin, RW, (2001) *Biotechnic & Histochemistry* 76(4):163–164.
Kanazawa et al., (1966) *J. Antibiotics* 19:229–233.
Liu, D. (1981) *Bull. Environ, Contam. Toxicol.* 26:145–149.
Miura et al., (1987) *Analytical Biochemistry* 164:482–487.
Shahangian et al., (1984) *Journal of Analytical Toxicology*, vol. 8, pp. 273–276.
Soyama et al., (1987) *Clinica Chimica Acta*, 168:259–260.
Winartasaputra et al., (1980) *Clin. Chem.* 26/5:613–617.
O'Brien, J., (2000) "Investigation of the Alamar Blue (Resazurin) Fluorescent Dye for the Assessment of Mammalian Cell Cytotoxicity," *European J. Biochemistry*, vol. 267, No. 1, pp. 5421–5426.
McMillan, M.K., (2002) "An Improved Resazurin Based Cytotoxicity Assay for Hepatic Cells," *Cell Biology and Toxicology*, vol. 18, No. 3, pp. 157–173.
Rasmussen, E., (1999) "Use of Fluorescent Redox Indicators to Evaluate Cell Proliferation and Viability," *In Vitro and Molecular Toxicology*, vol. 12, No. 1, pp. 47–58.
Ikawa et al., (1985), Measurement of th eRatio of Primary to Total Bile Acids in Serum by Enzymatic Fluorometric Microassay and Its Clinical Significance in Patients with Liver Disease, *Tohoku J. exp. Med.*, 145:185–195.

* cited by examiner

*Primary Examiner*—Ralph Gitomer
(74) *Attorney, Agent, or Firm*—Joseph T. Leone, Esq.; DeWitt Ross & Stevens S.C.

(57) ABSTRACT

Disclosed are a method and a corresponding kit for determining the cytotoxicity of a test agent. The method includes the steps of adding a pre-determined amount of the test agent to a vessel containing living cells in culture medium. The cells are then incubated for a pre-determined amount of time. To the cells and culture medium is then added a reagent mixture that is non-toxic to the living cells. In the preferred embodiment, the reagent mixture contains a solvent, a dye, an electron transfer agent, a substrate for a cytoplasmic enzyme having a half-life greater than two hours and NAD+. The contents of the vessel are then measured for production of the reduced state of the dye, the production of the reduced state of the dye being caused by a cytoplasmic enzyme specific for the substrate in the reagent mixture. In the preferred embodiment, the production of the reduced state of the dye is caused by lactate dehydrogenase released from dead and dying cells within the vessel. The kits contain components necessary for performing the method.

48 Claims, 5 Drawing Sheets

CYTOTOXICITY ASSAY

FIELD OF THE INVENTION

The invention is directed to assays for determining the cytotoxic effect of a given test compound or a given set of test conditions. The inventive method measures the release of a cytoplasmic component from dead and dying cells, the cytoplasmic component having a half-life in culture medium greater than two hours, and preferably greater than four hours at 37° C. The cytoplasmic component is measured by the conversion of an indicator dye. The preferred cytoplasmic component to be measured is lactate dehydrogenase (LDH), an enzyme that catalyzes the oxidation of lactate to pyruvate. Thus, in the preferred embodiment, an LDH-catalyzed oxidation of lactate is linked to a diaphorase-catalyzed reduction of a non-fluorescent species to yield a fluorophore. Kits for practicing the invention are also disclosed.

BACKGROUND

Methods to determine cell viability or cytotoxicity in response to exposure to a given test agent are key to pharmaceutical and environmental testing, pesticide and herbicide testing, drug discovery, etc. In short, to determine whether a given chemical agent presents a real or potential risk when exposed to a given cell type requires a method that reliably, precisely, and accurately measures cell toxicity and/or viability after exposure to the test agent.

A common method of determining cell viability is based on the ability of the membrane of viable cells to exclude vital dyes such as trypan blue and propidium iodide. Living cells exclude such vital dyes and do not become stained. In contrast, dead or dying cells that have lost membrane integrity allow these dyes to enter the cytoplasm, where the dyes stain various compounds or organelles within the cell.

Non-viable cells that have lost membrane integrity also leak cytoplasmic components into the surrounding medium. Cell death thus can be measured by monitoring the concentration of these cellular components in the surrounding medium. One such method is described in Corey et al. (1997) *J. Immunol. Meth.* 207:43–51. In this assay, the release of glycerldehyde-3-phosphate dehydrogenase (G3PDH) from dead or damaged cells is measured by coupling the activity of the released G3PDH to the production of ATP.

Other methods to test for cell viability or cell death rely upon the conversion of a dye from one state to another. For example, in a typical format, prior to the reaction the dye absorbs at a first wavelength of radiation. The dye is then converted to a product that absorbs at a second (and different) wavelength of light. By monitoring the conversion of the dye from one state to the other, the extent of cell viability or cell death can be determined. A number of suitable dyes for this purpose are known in the art. The most frequently used of these indicators are electron-acceptor dyes such as tetrazolium salts. Tetrazolium salts known in the prior art include MTT (3-(4,5-dimethylthiazol-2-yl)-2, 5-diphenyltetrazolium bromide), XTT (sodium 3'-{(1-phenylamino-carbonyl)-3,4-tetrazolium}-bis(4-methoxy-6-nitro)benzene-sulfonic acid hydrate), and MTS (3-(4,5-dimethylthiazol-2-yl)-5-(3carboxymethoxyphenyl)-2-(4-sulphophenyl)-2H-tetrazolium, inner salt).

A typical cell viability and proliferation assay using MTS has been described (Buttke et. al., (1993) *J. Immunol. Methods,* 157: 233–240). Dunigan et al. (1995, *BioTechniques,* 19:640–649) proceed to describe that one of the hallmarks of metabolism is the generation of energy via complex redox reactions of organic molecules. A great many of these reactions utilize β-nicotinamide adenine dinucleotide (NADH) or β-nicotinamide adenine dinucleotide phosphate (NADPH) as hydrogen donors. While it is theoretically possible to monitor NADH and NADPH concentrations directly via spectrophotometry, from a practical standpoint, direct spectrophotometric analysis is limited due to the presence numerous components that absorb light near the absorption maximum of NADH and NADPH ($\epsilon$=16,900 at $\lambda_{max}$ of 259 nm). For example, NAD+, NADP+, DNA, RNA, and most proteins have absorption maxima at approximately 260 nm.

Buttke et al. describe using MTS to measure indirectly the reduction caused by living, proliferating cells, MTS having an absorbance in the visible region when in its reduced form. The reduced, formazen form of MTS is water soluble and has a broad absorption maximum centered at 450–580 nm. The experiments described by Dunigan et al. are entirely cell free. MTS and MTS/phenazine methosulfate (PMS) solutions were prepared as stock solutions and various combinations of enzymes and reducing agents were added to aliquots of the stock solutions and analyzed spectrophotometrically over time. Various combinations of NADH, NADPH, dithiothreitol, 2-mercaptoethanol, malic acid, isocitric acid, malate dehydrogenase, and isocitrate dehydrogenase were tested. The authors found that MTS alone converts only very slowly to its reduced formazen structure. Reactivity of the MTS, however, is hugely accelerated by adding 5% of the electron transfer reagent PMS to the reaction solution. Thus, the authors conclude that MTS/PMS is a useful monitor of NADH and NADPH generation in cell-free aqueous systems.

Lancaster et al., U.S. Pat. No. 5,501,959, issued Mar. 26, 1996, describe a cell viability and proliferation assay wherein microorganisms, tissue cells, or the like, are incubated in a growth medium in the presence of the dye resazurin and a compound to be tested. A redox stabilizing agent, dubbed a "poising" agent, is also added to the reaction mix to inhibit non-specific autoreduction of the resazurin due to components found within most culture media. In this assay, the resazurin dye is reduced by the activity of living cells. Thus, in the Lancaster et al. assay, the resazurin dye is used as a redox indicator to detect microbial growth, not microbial death. The reduced form of resazurin, known trivially as resorufin, can be detected fluorimetrically or colorimetrically. Resazurin, the oxidized form of the dye, is blue, while resorufin, the reduced form of the dye, is red.

Several cytotoxicity assays can be purchased commercially. For example, Molecular Probes of Eugene, Oreg., markets a cytotoxicity assay kit under the trademark "Vybrant". The "Vybrant"-brand assay detects the release of the cytoplasmic enzyme glucose-6-phosphate dehydrogenase (G6PDH) from dead and dying cells. This assay detects G6PDH via a two-step process that leads to the reduction of resazurin to resorufin. Molecular Probes' product literature specifically states that incubations longer than 24 hours "will result in significant degradation of G6PDH, impairing the assay results." See Molecular Probes' product information flier no. V-23111, revised Oct. 22, 2001. In the hands of the present inventors, however, the half-life of the G6PDH following cell lysis at 37° C. was estimated to be less than two hours at 37° C., thus rendering this kit unsuitable for cytotoxic testing over longer spans of time.

Promega Corporation of Madison, Wis., markets a line of cell viability, cytotoxicity, and cell proliferation assays under the trademarks "CellTiter 96", "CellTiter-Glo", and "CytoTox 96." See Promega Technical Bulletin Nos. 112, 169, 245, and 288. Promega's "CytoTox 96"-brand non-radioactive cytotoxicity assay, for example, is a colorimetric assay for determining the cytotoxicity of a test compound. This assay quantitatively measures the release of LDH from dead cells using an enzyme-linked reduction of INT, an MTS-like tetrazolium dye (see U.S. Pat. No. 5,185,450 for full description of the MTS dye). This assay is a two-step protocol (ie., it is non-homogeneous) and the INT dye is detected colorimetrically. This assay uses conditions that are incompatible with living eukaryotic cells as the reaction takes place at a pH of 8.5 with a detergent (Triton-X100) present.

Genotech of St. Louis, Mo., markets a lactate dehydrogenase (LDH)-based cytotoxicity assay under the trademark "CytoScan". The "CytoScan"-brand assay is a colorimetric method that measures LDH released from dead cells. The LDH released by dead cells is measured via a coupled enzymatic reaction that results in the reduction of a tetrazolium salt into a red-colored formazen. The LDH activity is then determined as a function of NADH oxidation or tetrazolium reduction over a defined period of time. See Genotech catalog no. 786-210. Essentially identical assay kits are marketed by Panvera of Madison, Wis. (LDH Cytotoxicity Detection Kit, Panvera product no. TAK MK401), Oxford Biomedical Research of Oxford, Mich. (Colorimetric Cytotoxicity Assay Kit, Oxford product no. LK 100), and Roche Molecular Biochemicals of Indianapolis, Ind. (Cytotoxicity Detection Kit, Roche catalog no. 1 644 793). All of these kits require a two step procedure to remove culture medium to a separate container and thus are non-homogeneous.

Sigma of St. Louis, Mo., markets two different in vitro toxicology assay kits under the Product Names "Tox-7" and "Tox-8". The "Tox-7" kit is LDH-based and is essentially identical to Genotech's "CytoScan"-brand assay described in the preceding paragraph. The "Tox-7" assay is a two-step process that requires transferring a supernatant or a cell lysate to a separate vessel, where the supernatant or lysate is then analyzed. Two-step processes are not preferred for high-throughput screening due to the increased material handling requirements. The particular tetrazolium dye used in Sigma's "Tox-7" kit is not specified, but the product literature indicates that the reaction is measured spectrophotometrically at 490 nm, the absorption maximum typical for formazans (and the same wavelength specified in the Genotech product).

All of these commercially available kits require transfer of culture supernatant to an additional vessel for enzymatic measurement of LDH activity and are therefore non-homogeneous.

In Sigma's "Tox-8" assay, bioreduction of resazurin by viable cells (not dead cells) results in the formation of resorufin. The amount of dye reduced can be measured fluorimetrically or spectrophotometrically.

BioSource, International (Camarillo, Calif.) markets kits for measuring cell proliferation and viability under the trademark "alamarBlue," (see catalog nos. DAL1025 and DAL1100). Like resazurin, "alamarBlue"-brand dye can be used to monitor the reducing environment of living cells. The technology underlying this commercial product is described in Lancaster, U.S. Pat. No. 5,501,959.

The use of absorbent pads impregnated with resazurin and antibiotics for antimicrobial susceptibility testing are described in Baker et al. (1980) *Microbiol.* 26:248–253 and Canadian Patent No. 1,112,140. Bacterial isolates are applied to the pad in a brain heart infusion broth. The protocols described, however, are not suitable for determining minimum inhibitory concentrations (MIC). Kanazawa et al. (1966) *J. Antibiotics* 19:229–233 also describe the use of absorbent pads impregnated with resazurin and antimicrobial agents for use in susceptibility testing. Brown et al. (1961) *J. Clin. Path.* 5:10–13 and U.S. Pat. No. 3,107,204 describe the use of absorbent pads impregnated with a tetrazolium redox indicator and antimicrobial agents, also for use in susceptibility testing.

There remains, however, a long-felt and unmet need for a cytotoxicity assay that measures cell death (rather than viability), wherein the assay is rapid, the components are non-toxic (and thus the test can be run in the presence of the cells being investigated), and wherein the cytoplasmic components measured have a half-life greater than about two hours.

SUMMARY OF THE INVENTION

In recognition of the above-described shortcomings, a first embodiment of the invention is directed to a method for determining the cytotoxicity of a test agent. The method comprises first adding a pre-determined amount of the test agent to a vessel containing living cells in culture medium. The cells are then incubated in the culture medium for a pre-determined amount of time. To the incubated cells and culture medium is then added a reagent mixture that is non-toxic to the still-living cells in the culture medium. The reagent mixture comprises a solvent, a dye having an oxidized state and a reduced state wherein the reduced state can be distinguished from the oxidized state and wherein the dye is initially present in the oxidized state, an electron transfer agent, a substrate for a cytoplasmic enzyme having a half-life greater than two hours and a cofactor for the cytoplasmic enzyme. The contents of the vessel are then measured for production of the reduced state of the dye. The reduced state of the dye is produced by a cytoplasmic enzyme that will convert the substrate included in the reagent mixture to the desired product. The cytoplasmic enzyme is released from dead and dying cells within the vessel, but may also be present as a component in the cell medium such as serum. Thus, by quantifying the amount of this enzyme indirectly (by detecting the reduced state of the dye) and subtracting background amounts present before cell compromise takes place, cell death caused by the test agent is determined.

The invention also encompasses kits to carry out the above-described method. The reagent mixture that is used in the method (and provided in the kit) can be added directly to the culture medium (with the cells present) without adversely affecting cell viability for the duration of the assay. In the preferred embodiment, the method and the corresponding kit yield results essentially immediately, generally in about 10 minutes. Data can be gathered either colorimetrically or fluorimetrically. Fluorometric measurement is much more sensitive and is the preferred means of resorufin detection. In other embodiments, data can be collected very quickly after addition of the reagent mixture, with the data gathering process generally being possible in a matter of seconds or minutes.

It is much preferred that the entire method be conducted in a single vessel. That is, the cells are placed into a vessel containing suitable medium. The test agent is added to the vessel. The vessel with the cells and the test agent is incubated. The reagent mixture is then added to the same vessel, in the presence of the incubated cells (rather than taking a cell-free aliquot and adding the reagent mixture to it). The cell medium is then measured (colorimetrically or fluorimetrically). The preferred embodiment of the invention is thus "homogeneous," homogeneous designating that the entire method is conducted in a single vessel, rather than requiring aliquots to be transferred and tested in a different vessel. This makes the present method very highly suitable for high-throughput automation, where it is desirable that material handling and manipulation requirements be reduced to an absolute minimum.

As noted above, the output from the method begins to occur essentially immediately after adding the reagent mixture to the incubated cells. Thus, data gathering can begin promptly after adding the reagent mixture. The signal generated by the method may be measured for anywhere from a matter of seconds, to ten minutes, to thirty minutes or longer. In the preferred embodiment, the signal is measured following a period of time generally on the order of 10 minutes.

In the preferred embodiment of the method, the substrate for a cytoplasmic enzyme having a half-life greater than two hours is lactate, and the cytoplasmic enzyme that forms the basis of the cytotoxic measurement is lactate dehydrogenase (LDH). LDH has a half-life of approximately 9 hours in culture medium at 37° C. following cell lysis. The preferred dye for use in the invention is resazurin. MTS may also be used. The preferred electron transfer agent is the enzyme diaphorase, although Meldola's Blue also may be used.

It is also preferred that a stop solution (preferably a solution of sodium dodecylsulfate, SDS) be added to the reaction prior to measuring for production of the reduced state of the dye.

The present method relies upon cytoplasmic components that have a long half-life after release from dead and dying cells. Thus, as noted above, in LDH is the cytoplasmic component measured. Because the method utilizes a cytoplasmic component with a relatively long half-life, minimal degradation of the component will occur over a test period that may include incubation times of 12 or 24 hours (or longer). The activity of the released cytoplasmic component with a long half-life can be measured more reliably than a released component with a short half-life, especially when the incubation period of the cells with the test agent results in release of the cytoplasmic component several hours before the reagent mixture is added to the vessel.

It is much preferred, although not required, that the method be performed in a "homogenous" fashion, meaning that all of the steps of the method are carried out in the same vessel, in the presence of the cells being used in the method. This can be done, for example, in a test tube, a multi-well plate, or any other suitable vessel.

A second embodiment of the invention is directed to a kit for carrying out the above-described method. The kit comprises, in combination, a dye disposed in a first container, the dye having an oxidized state and a reduced state wherein the reduced state can be distinguished from the oxidized state and wherein the dye is present in the oxidized state; a lyophilized substrate mix disposed in a second container, the substrate mix comprising an electron transfer agent, a substrate for a cytoplasmic enzyme having a half-life greater than two hours, and a cofactor for the cytoplasmic enzyme; and (optionally) instructions for use of the kit.

In the preferred embodiment of the kit, the reagent mix is an aqueous solution comprising: about 109 mM lactate; about 3.3 mM NAD+; about 2.2 U/ml diaphorase about 3.0 mM Tris buffer; about 30 mM HEPES; about 10 mM NaCl; and about 350 $\mu$M resazurin. Other component concentrations may be used to the extent that the substrate, the cofactor and the electron transport agent are present in excess so that there is a suitable rate of reaction and to the extent that the osmolality of the reagent mix does not adversely affect the overall osmolality of the culture medium to the point that the cells are damaged.

Optionally, a stop solution may be disposed in a third container. The stop solution generally comprises a soap, a detergent, or a strong base. Preferred stop solutions include SDS or sodium hydroxide.

Also optionally, a lysis solution (for positive control experiments) may be disposed in an additional (fourth) container. Preferred lysis solutions include 9% w/v Triton X-100 in water.

Another embodiment of the kit may contain a reagent mixture in a single container. Such kits comprise, in combination, a buffer, a dye, a substrate for the cytoplasmic component, an appropriate cofactor for the cytoplasmic component, and an electron transfer agent, all disposed in a first container. For example, such a first container would contain, in combination, resazurin, lactate, NAD+, diaphorase, Tris, HEPES and NaCl. The kit also contains instructions for the kit, and optionally, a stop solution.

A primary advantage of the preferred embodiment of the present invention is that it provides improved media and methods that employ resazurin or MTS as an indicator of cell death. In particular, the inventive method utilizes a reagent mixture that is not deleterious to the viability of the cells being tested. Thus, the inventive method is "homogeneous" in that it can be performed in the same vessel in which the cells are incubated, without the need to remove a cell-free aliquots of the culture medium. In short, using the present invention, there is no need to draw a cell-free aliquot of the cell culture medium and run the test on the aliquot. The method can be performed directly upon the cell medium, in the presence of the incubated cells, in the same vessel in which the cells were incubated.

Another advantage of the invention is that, in the preferred embodiment, it measures the activity of LDH to determine cell death. Because LDH has a long half-life (greater than 8 hours at 37° C.), the invention can be used to determine the extent of cell death over a long testing period, more accurately and more precisely than prior art methods.

Another advantage of the invention is that because the assay conditions are not deleterious to the cells being tested, the living cells present in the culture when the assay is performed generate no more than an insignificant amount of signal above the background. This is because the cell membranes of the viable cells are not damaged by the reagent solution used in the method, and thus these viable cells retain their cytoplasmic LDH. Therefore, only LDH present in the medium, from a medium additive such as serum or released from membrane-compromised cells, is measured. This allows the assay to be performed directly in vessels containing viable cells.

The utility of the assay is manifest in that determining the cytotoxicity of a given compound or composition is a critical piece of information in the drug discovery process. For example, cytotoxicity is desirable when the toxicity is specifically displayed against an identified target cell type, such as a given type of cancer, an infectious, disease-causing microorganism, or a parasitic organism. Cytotoxicity, of course, is undesirable when, for example, a putative new drug is discovered to be cytotoxic to normal cells. The subject invention can be used in both instances to measure the cytotoxicity of a given test agent against a given cell type.

DETAILED DESCRIPTION OF THE INVENTION

The following abbreviations are used throughout the specification and claims. Words not expressly defined herein are to be given their normal and accepted meaning in the art.

"L929 cells"=a fibroblastoid adherent cell line derived from C3H/An mouse subcutaneous areolar and adipose tissue, available commercially from the American Type Culture Collection (Manassas, Va.) under accession no. ATCC CCL-1.

"Jurkat cells"=a human lymphocyte T-cell line, available commercially from the ATCC under accession no. ATCC TIB-152.

"HEPES"=N-2-hydroxyethylpiperazine-N'-2-ethanesulfonic acid.

"Known or putative pharmaceutical or therapeutic agent"=a chemical compound or formulation known and used as a pharmaceutical agent, or a chemical compound or formulation being investigated for use as a pharmaceutical agent.

"LDH"=lactate dehydrogenase.

"MTS"=3-(4,5-dimethylthiazol-2yl)-5-(3-carboxymethoxyphenyl)-2-(4-sulphophenyl)-2H-terazolium, inner salt, available commercially from Promega Corp, Madison, Wis.

"MTT"=3-(4,5-dimethylthiazol-2-yl)-2,5-diphenyltetrazolium bromide, available commercially from Aldrich.

"NADH"=β-nicotinamide adenine dinucleotide (protonated form). "NAD+" indicates unprotonated form.

"NADPH"=β-nicotinamide adenine dinucleotide phosphate (protonated form). "NADP+" indicates unprotonated form.

"resazurin"=7-hydroxy-3H-phenoxazin-3-one 10-oxide (sodium salt), available commercially from Aldrich (catalog no. 19,930-3).

"resorufin"=7-hydroxy-3H-phenoxazin-3-one (the reduced form of resazurin), available commercially from Aldrich (catalog no. 42,445-5).

"SDS"=sodium dodecylsulfate.

"Tris"=tris(hydroxymethyl)aminomethane.

"Vessel"=indicates any container or holder wherein the inventive method can occur. Includes single well containers, such as test tubes, and multi-well containers such as microtiter plates of any configuration. "Vessel" also encompasses pads, patches, tapes, bandages, and the like, of any material construction, that are sufficiently absorbent to retain the cells and reagents needed to perform the subject method.

"XTT"=sodium 3'-{(1-phenylamino-carbonyl)-3,4-tetrazolium}-bis(4-methoxy-6-nitro)benzene-sulfonic acid hydrate.

Figure 1:
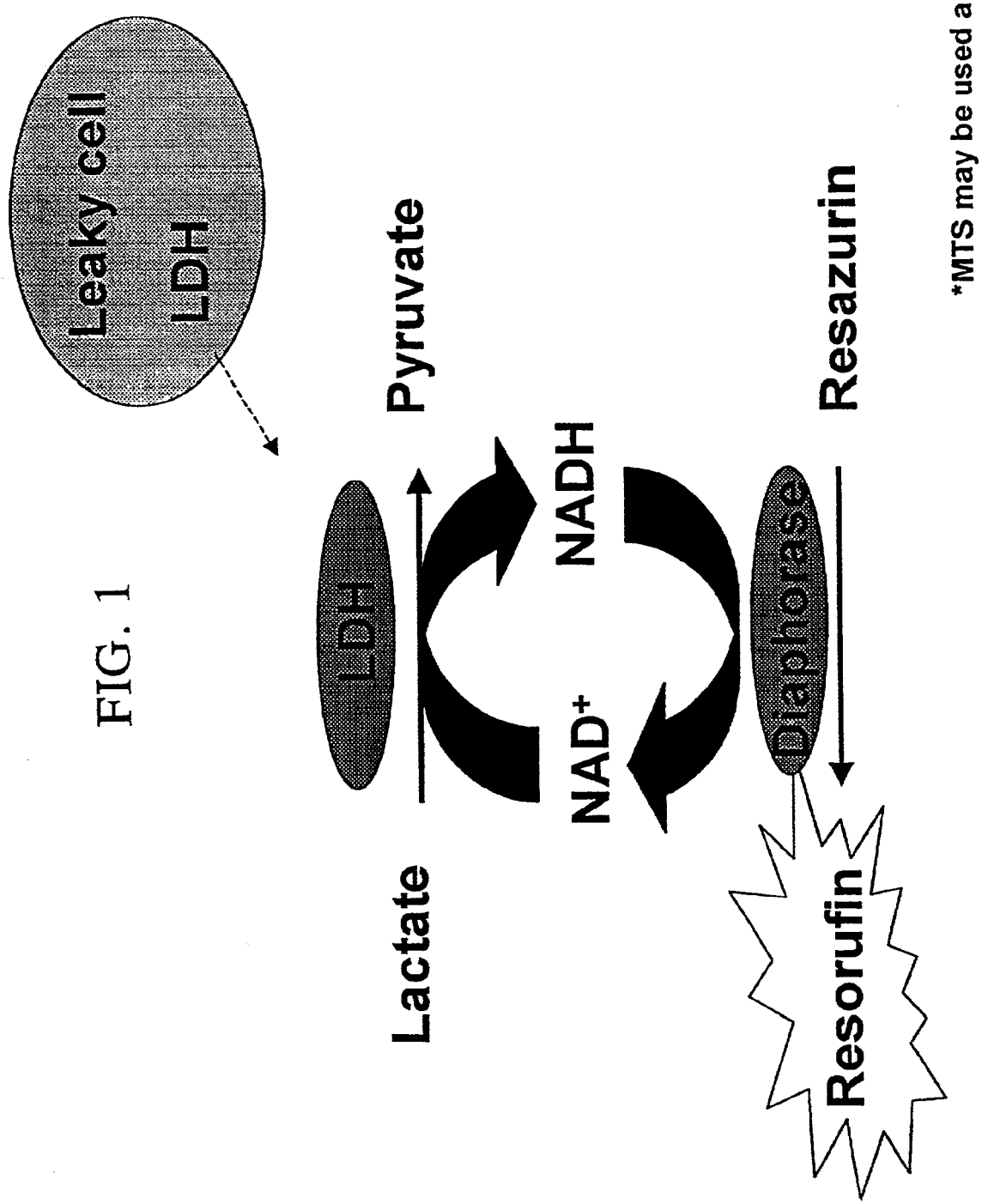
FIG. 1 is a schematic rendering of the preferred method according to the present invention.

Referring now to FIG. 1, which is a schematic diagram of the preferred method according to the present invention, the method comprises incubating cells in a growth medium and an agent to be tested (hereinafter referred to as the test agent). The cells are then incubated in the presence of the reagent mixture and the test agent for a period of time. Assuming the test agent, not shown in FIG. 1, is at least partially cytotoxic, this will cause some cells to die and become "leaky", thereby releasing cytoplasmic components, such as LDH, into the culture medium.

The reagent mixture used in the method is non-toxic to the living cells. Thus it can be added directly to the cells being incubated, without adversely affecting the outcome of the method. The reagent mixture comprises a solvent (preferably water, and preferably buffered), a dye having an oxidized state and a reduced state wherein the reduced state can be distinguished from the oxidized state and wherein the dye is initially present in the oxidized state, an electron transfer agent, a substrate for a cytoplasmic component (such as lactate, a substrate specific for LDH), and an appropriate cofactor (such as NAD+ for LDH). As indicated in FIG. 1, the dye preferably is resazurin, although the tetrazolium dye MTS can also used with success. Other redox indicators may also be used. The preferred electron transfer agent is the enzyme diaphorase, but Meldola's Blue (also known as naphthol blue, color index C.I.51175) (EM Science/Harleco, a division of Merck KGaA, Darmstadt, Germany) may also be used.

In the preferred embodiment, the cells are incubated for a pre-determined amount of time in the presence of the test agent, after which time the reagent mixture is added to the incubated cells. As shown in FIG. 1, when lactate is used as the substrate, and LDH is the cytoplasmic component being measured, LDH released from dead or dying cells initiates an enzyme-catalyzed series of reactions. In the first reaction, lactate (one of the ingredients included in the reagent solution) is oxidized to form pyruvate. This reaction requires NAD+ and thus, in the preferred embodiment, NAD+ is included in the reagent mixture.

The oxidation of lactate to pyruvate results in the production of NADH. In a second reaction, the dye (resazurin is shown in FIG. 1) is reduced in a reaction powered by the NADH produced in the first reaction and catalyzed by the electron transfer agent (in FIG. 1, diaphorase, the preferred electron transfer agent, is shown). Thus, as illustrated in FIG. 1, the preferred electron transfer agent diaphorase catalyzes the reduction of resazurin to resorufin, a reduction powered by NADH.

The end result is a method wherein the release of a cytoplasmic component (LDH is shown in FIG. 1) from dead and dying cells is measured indirectly by measuring the reduction of a dye, that reduction being driven via a reaction that is linked to the oxidation of a substrate specific for the released cytoplasmic component (e.g., the lactate to pyruvate conversion caused by the released LDH as shown in FIG. 1). The amount of the reduced dye formed is proportional to the number of lysed cells. (See the Examples below for a further discussion.)

The production of the reduced form of the dye can be measured colorimetrically or fluorimetrically, or other electromagnetic spectral measuring device, depending upon the dye. Resorufin can be measured either colorimetrically or fluorimetrically, however, MTS can only be measured colorimetrically. Suitable measuring devices are exceedingly well known in the art and can be purchased from a host of commercial suppliers.

In particular, when the dye used is resazurin, reduction can be detected either by absorbance colorimetry or by fluorimetry. Resazurin is deeply blue in color and is essentially non-fluorescent, depending upon its level of purity. Resorufin, the reduced form of resazurin, is red and very fluorescent. When using colorimetry, the reaction is monitored at wavelengths well known in the art to be an absorption maximum for resorufin (approximately 570 nm). Fluorescence measurements of resorufin are made by exciting at wavelengths well known in the art (approximately 530 to 560 nm) and measuring the emission spectrum (known to the art to have a maximum at about 590 nm). Because fluorometric detection is more sensitive than spectrophotometric detection, in the preferred embodiment of the method, resazurin is used as the dye and the production of resorufin is detected fluorimetrically.

The medium in which the cells are grown or held does not limit the functionality of the invention, although non-reducing media are preferred to minimize any non-specific reduction of the dye. For microbial cultures, suitable media include, without limitation, Mueller-Hinton Broth and trypticase soy broth. For mammalian cell cultures, suitable media include, without limitation, RPMI 1640, RPMI 1640 plus fetal bovine serum, and Dulbecco's Modified Eagle Medium, Hanks' Balanced Salt Solution, Phosphate Buffered Solution. It has been observed that media naturally containing or supplemented with sodium pyruvate slows the rate of the LDH reaction and thus the rate of resorufin generation. Depending upon desired sensitivity, longer development times may be desired.

In one application of the method, the test agent will be a putative growth-inhibiting substance, such as an antimicrobial agent or a cytotoxic drug. The nature of the test agent, however, is virtually unlimited. The test agent could be, for example, any element, compound, mixture, drug, or putative drug, in any form (such as solid, liquid, or gas) or a set of environmental conditions (such as any combination of heat, humidity, light, oxygen level, and the like) desired to be tested for its cytotoxic effects. The method can also be used to test known antimicrobial agents and cytotoxic drugs for the purpose of determining which chemotherapeutic agents would be most effective against a given infection or cell type. The method can also be utilized with unknown or suspected antimicrobial agents and drugs for the purposes of determining their potential activity against a given microorganism or cell type, e.g., high-throughput screening of substances for biological activity as part of drug screening or other activities.

Cells to be used in the method may be collected from any source, and may be eukaryotic or prokaryotic. For example, human cells may be collected by doctors in their offices and sent to a central testing laboratory for testing using the present method, or cell specimens may be collected from patients in a hospital. The microorganism specimens may come from any part of the human or animal body, such as from cerebral spinal fluid, an abscess, an infected wound, genital infections, etc. The cells may be from tumor biopsies or other specimens. The cells to be tested may also come from food samples, soil samples, etc. In short, the nature of the cells to be tested and their source is not critical to the invention.

The collected specimens are cultured on or in a suitable medium, as noted above, in accordance with conventional laboratory practice. From the bacterial colonies or cellular clones on the primary culture plate, an inoculum is prepared in accordance with an established procedure which produces a bacterial or cellular suspension of a prearranged concentration. Further processing of the suspension depends on the particular apparatus and method to be used for susceptibility testing.

One preferred outcome of bacterial testing is to generate information on the probable success of treating a given population with a selected antibiotic. Another use of the invention is to test for the presence of microbes in a mixture, solution or on a surface thought to be free of them. The purpose of cellular cytotoxicity testing may be to determine the susceptibility of the tumor cells to particular chemotherapeutic drugs or test agents, or for screening potential drug candidates, or to determine whether a given drug candidate exhibits undesirable cytotoxicity to normal cells or any indicator cell type.

The method described herein is inherently quantitative in that the amount of the reduced form of the dye produced is proportional to the number of cells lysed. The method, however, can be used both for quantitative testing and qualitative testing. The term qualitative testing refers to testing apparatus and methods which produce test results that generally indicate whether an organism or cellular specimen is sensitive or resistant to a particular antibiotic or cytotoxic test agent. The relative degree of sensitivity or resistance is not reported in qualitative testing. The term quantitative testing refers to testing apparatus and methods which produce test results that provide data on the concentration of the antimicrobial or cytotoxic product that will be sufficient to inhibit growth of the microorganism or other cell type. Typically, for microorganism specimens, six or more different dilutions of the test agent are utilized, covering the therapeutic range of concentrations of the test agent. The term minimum inhibitory concentration (MIC) is often used to refer to the result provided by quantitative testing of a test agent and is defined as the minimum concentration of the test agent that will produce inhibition of the growth of the cells used in the method.

The general protocol of the method proceeds as follows:

First, a lyophilized substrate mixture is reconstituted in a buffer and allowed to equilibrate to assay temperature (usually room temperature). This yields a reagent mixture that contains all of the required components to perform the method.

The reagent mixture is then added to the sample(s) to be measured, the samples having been previously incubated for a pre-determined time in the presence of known concentrations of the test agent. The samples are then gently mixed to ensure uniformity. The samples are then incubated for a predetermined amount of time, preferably about ten minutes, prior to gathering the fluorescent or colorimetric data.

The reactions are stopped by the addition of a suitable stop reagent, preferably 3% w/v SDS in water or an aqueous solution of sodium hydroxide (1 N).

The fluorescence of the reduced form of the indicator dye, preferably resorufin, is then recorded. The amount of fluorescence is indicative of the quantity of cytoplasmic component (e.g., LDH) activity present in the sample. The preferred filter set for fluorescent recording measures excitation at 560 nm and emission at 590 nm. Other slight variations from these wavelengths are possible.

If resazurin is used as the dye and fluorescence is the endpoint measured, the vessel in which the reaction is performed, such as microtiter assay plate, should be compatible with a micro-well fluorimeter. If MTS is used as the indicator, the vessel in which the reaction is performed should be compatible with 490 nm absorbance measurements.

The present invention is also drawn to kits that contain reagents and instructions necessary to carry out the above methods. In its most preferred form, the kit includes an assay buffer containing a dye (again, the dye having an oxidized state and a reduced state wherein the reduced state can be distinguished from the oxidized state and wherein the dye is present in the mixture in primarily the oxidized state) disposed in a first container. The kit also includes a lyophilized substrate mix containing an electron transfer agent, a substrate for a cytoplasmic component (e.g., lactate) and an appropriate cofactor for the cytoplasmic enzyme (e.g., NAD+ in the case of LDH) disposed in a second container. An optional third container may hold a stop solution. An optional additional container may hold a lysis solution. The kit should also include instructions for how to use the kit.

It is preferred that the substrate mixture be present in the form of a lyophilized powder that is then reconstituted with a buffer to yield a reagent mix that is non-toxic to cells and which contains the components required to practice the method of the present invention. This embodiment is preferred because the lyophilized substrate mix is easier to store and transport. The kit, however, may also be configured so that the necessary components listed above are packaged in the form of a pre-made reagent mix, ready for use.

In the preferred embodiment of the kit, the dye is resazurin or 3-(4,5-dimethylthiazol-2-yl)-5-(3-carboxymethoxyphenyl)-2-(4-sulphophenyl)-2H-tetrazolium, inner salt (MTS). It is also preferred that the substrate for the cytoplasmic enzyme is lactate. It is preferred that the electron transfer agent be an enzyme, most preferably diaphorase. If LDH is the cytoplasmic enzyme measured, it is also preferred that the reagent mixture further contain NAD+ as the cofactor.

Thus, when the substrate mixture is reconstituted into a reagent solution, it is preferred that the reagent solution comprises an aqueous solvent, lactate (e.g., lithium lactate), NAD+, diaphorase, Tris buffer, HEPES, NaCl and resazurin or MTS. More specifically, when the substrate mixture is reconstituted, it is preferred that the reagent solution contain the following components: from about 50 mM to about 250 mM lithium lactate; from about 0.1 U/ml to about 10 U/ml diaphorase; from about 0.5 mM to about 10 mM NAD+; from about 1 mM to about 10 mM Tris buffer; from about 10 mM to about 100 mM HEPES; from about 1 mM to about 100 mM NaCl; and from about 50 $\mu$M to about 500 $\mu$M resazurin. These components are present in a manner that is consistent with the required osmolality of the cells under investigation (about 310 mOsm for most mammalian cell types). Optimization of kinetics may be necessary, and are well within the skills of the typical artisan.

In the most preferred embodiment, the substrate mixture, when reconstituted, yields a reagent solution comprising the following components: about 109 mM lithium lactate; about 3.3 mM NAD+; about 2.2 U/ml diaphorase; about 3.0 mM Tris buffer; about 30 mM HEPES; about 10 mM NaCl; and about 350 $\mu$M resazurin.

It is preferred that when the substrate mixture is reconstituted (or if the components are presented in the form of a ready-made solution), that the solution have a pH of from about 7.0 to about 8.0, more preferably from about 7.25 to about 7.60.

The stop solution of the kit preferably is an aqueous solution of a soap, detergent, or a strong base such as sodium hydroxide. The preferred stop reagent is a 1% to 5% solution of SDS or sodium hydroxide (preferably 1N). A 3% solution of SDS is preferred.

EXAMPLES

The following Examples are provided for illustrative purposes only. The Examples are included solely to aid in a more complete understanding of the invention described and claimed herein. The Examples do not limit the scope of the invention in any fashion.

Example 1

Demonstrating Background and Linearity:

A reagent solution was prepared combining a lyophilized substrate mixture with the assay buffer containing resazurin, and all of the ingredients required to measure the release of LDH from dead cells. The buffer solvent used to reconstitute the lyophilized substrate mixture was designed so that when it is used to reconstitute the mixture, the resulting solution has an osmolarity that is compatible with living cells. That is, the resulting solution was isotonic with the cells. When used to reconstitute the lyophilized substrate mix, the reagent solution contained:

| | |
|---|---|
| lactate: | 109 mM |
| NAD+: | 3.34 mM |
| diaphorase: | 2.17 Units/ml |
| Tris buffer: | 3.05 mM |
| HEPES: | 30 mM |
| NaCl: | 10 mM |
| resazurin: | 350 $\mu$M |

L929 cells were cultured in F-12/DME with 10% FBS and serially-diluted in a microtiter plate to yield duplicate wells containing approximately 0, 1562, 3125, 6250, 12,500, 25,000, and 50,000 cells per well, in 90 $\mu$l total volume. Cells were incubated at 37° C. for sufficient time to allow attachment (about 1.5 hours). Microtiter plactes containing cells were then removed from the incubator and in one set of wells, 10 $\mu$l of Triton X-100 (a lysing agent) was added and lysis was allowed to proceed to completion (about 30 minutes), while the cells equilibrated to room temperature. The other set of wells was left unlysed; 10 $\mu$l of phosphate buffered saline (PBS) was added to these as a volume control. Assay reagent mixture was prepared as previously described, and allowed to equilibrate to room temperature. After lysis was complete, 100 $\mu$l of reagent mixture was added to each well. The two sets of wells were allowed to incubate for 10 minutes. After 10 minutes, 50 $\mu$l of a stop solution (3% SDS) was added to each well. The fluorescence of each well was then measured (excitation 560 nm, emission 590 nm). The results are shown in FIG. 2.

Figure 2:
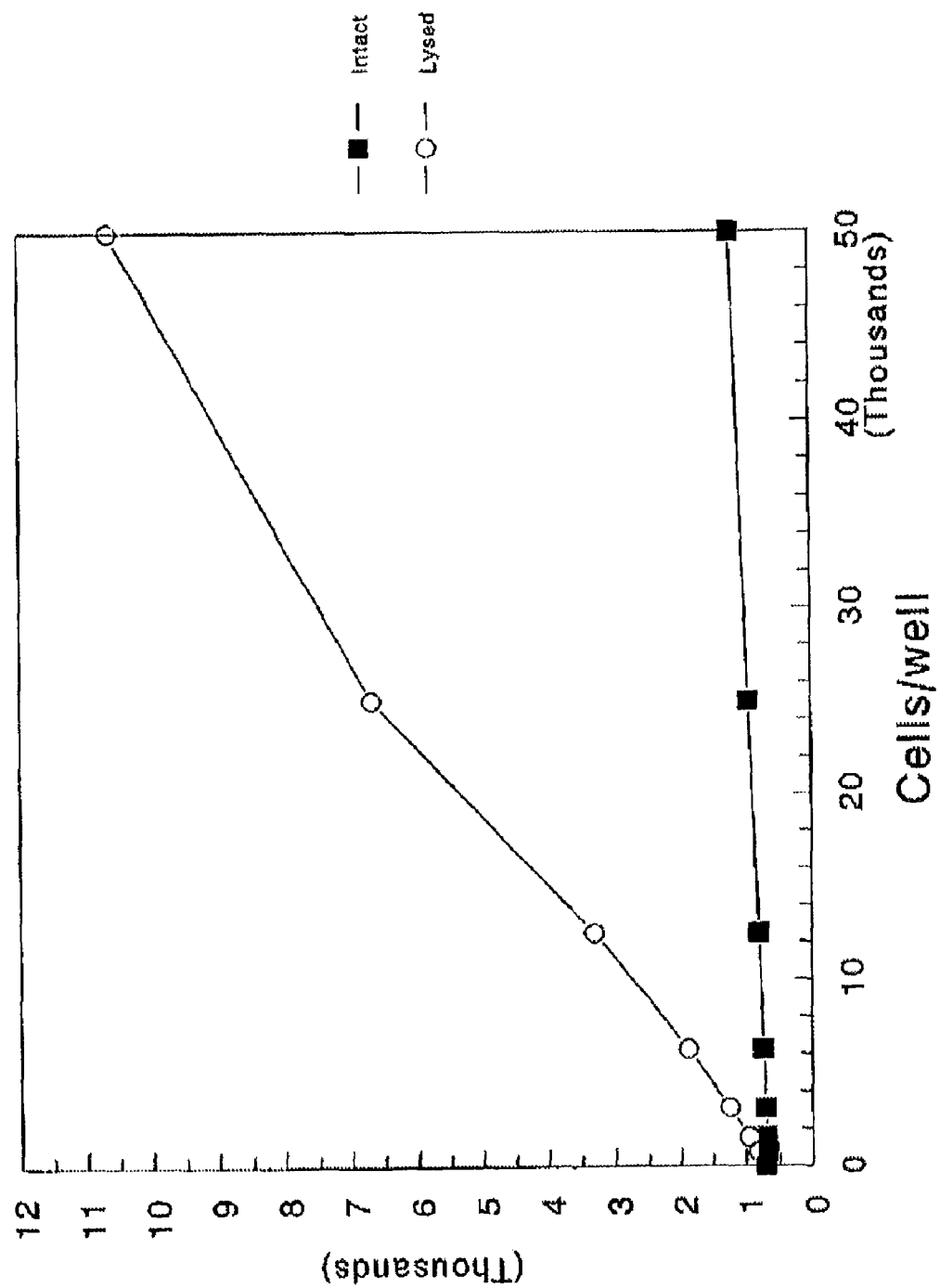
FIG. 2 is a graph depicting cell number (X-axis) versus the fluorescence (560 nm excitation and 590 nm emission) (Y-axis) for an exemplary run of the present method. The test was performed using L929 cells (ATCC CCL-1). Intact cells (■), lysed cells (○).

As can be seen from FIG. 2, in the wells where no lysing agent was present, a minimal background amount of fluorescence was detected. In the wells where the lysing agent was added, the fluorescence rises in a linear fashion, proportional to the number of cells in each well. As can be seen from FIG. 2, the method yields linear results from 0 to at least 500 cells per well to at least 50,000 cells per well. Other cell lines have been tested and show similar results.

This Example shows that the subject method can be used to calculate the cytotoxicity of a test agent because the amount of fluorescence detected is known to be proportional to the number of cells lysed.

Example 2

Stability of LDH in Culture Medium Compared to Stability of G6PDH

Figure 3:
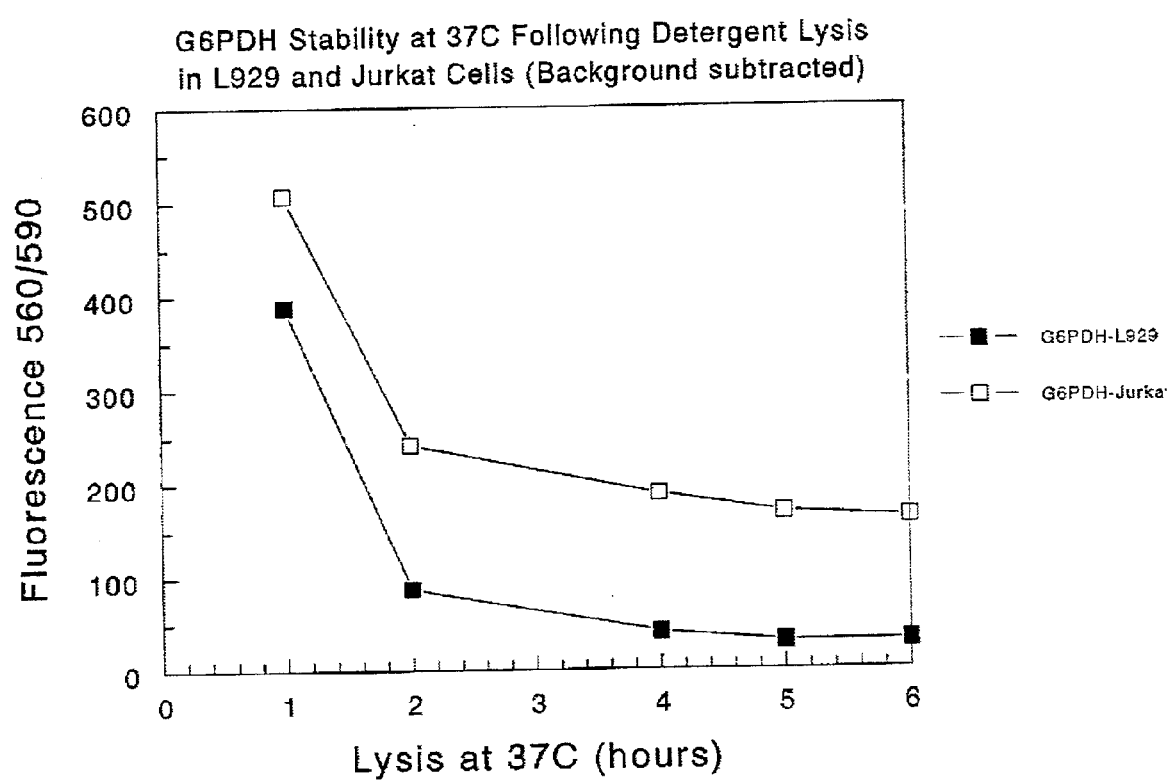
FIG. 3 is a graph depicting time after start of lysis in hours (X-axis) versus the fluorescence (560 nm excitation and 590 nm emission) (Y-axis) in an assay measuring the activity of G6PDH released from lysed L929 cells (■) and Jurkat cells (□).
Figure 4:
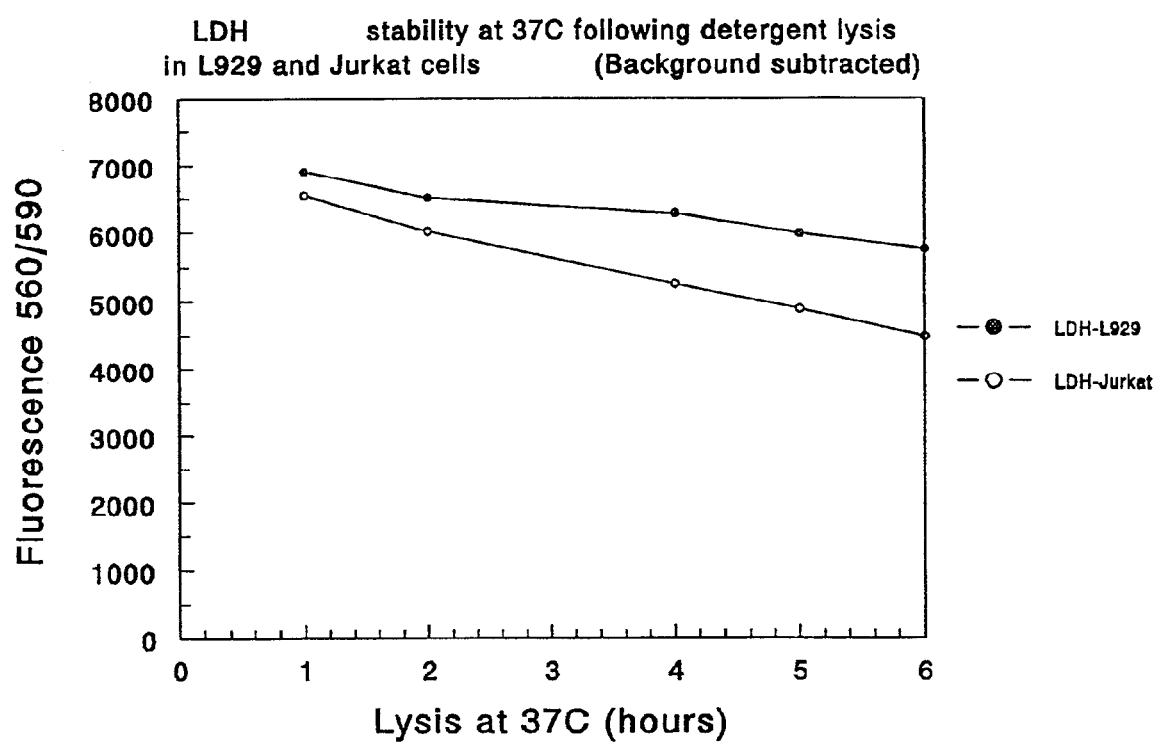
FIG. 4 is a graph depicting time after start of lysis in hours (X-axis) versus the fluorescence (560 nm excitation and 590 nm emission) (Y-axis) in an assay measuring the activity of LDH released from lysed L929 cells (●) and Jurkat cells (○).

FIGS. 3 and 4 depict the activity of glucose-6-phosphate dehydrogenase (G6PDH) (FIG. 3) and lactate dehydrogenase (LDH) (FIG. 4) in culture medium under identical assay conditions for two different cell types, L929 cells and Jurkat cells. The assay conditions used were similar to those listed above in Example 1. For measurement of G6PDH, glucose-6-phosphate and NADP+ were substituted for lactate and NAD+ and the concentration of resazurin was reduced to 250 $\mu$M to help increase the rate of resorufin development. Previous work with this G6PDH reagent indicates that fluorescence is proportional to the number of cells lysed. The L929 cells and Jurkat cells samples to be tested were assembled, and a lysing agent was added. To monitor stability of the released cytoplasmic enzymes, cells were maintained at 37° C. following addition of the lysis detergent. The amount of fluorescence was then measured at 1, 2, 4, and 6 hours from the time the lysing agent was added. FIGS. 3 and 4 thus depict the stability of LDH in culture medium as compared to the stability of G6PDH under the same conditions. As can be seen from FIG. 4, even 6 hours after adding the lysing agent, the LDH released from both L929 cells and Jurkat cells retains well over 50% of its starting activity. In sharp contrast, as can be seen from FIG. 3, G6PDH under the identical conditions, loses more than 50% of its starting activity within 2 hours of adding the lysing agent.

This Example shows that in the preferred embodiment of the present invention, the method relies upon an enzyme, LDH, whose half-life in culture medium is greater than 8 hours. Thus, the present invention can be used to measure cytotoxicity over longer incubation periods than assays known prior to the current disclosure.

Example 3

Measuring the Cytotoxicity of TNFα Using the Present Invention

L929 cells (2000 cells/well) were prepared using a 384-well tissue culture plate in F-12/DME medium supplemented with 10% horse serum. The cells were allowed to attach and grow for 24 hours at 37° C., 5% $CO_2$. Various concentrations of TNFα (n=4) in the presence of actinomycin D (1 $\mu$g/ml final) were added to the wells and the plate was then incubated for 20 hours. An equal volume of reagent (25 $\mu$l/well) was then added and the plate was shaken for 30 seconds. The plate was incubated for 10 minutes at 22° C., after which 12.5 $\mu$l/well of 3% SDS solution was added to stop the reaction. Fluorescence was then determined at 560 nm excitation and 590 nm emission.

Figure 5:
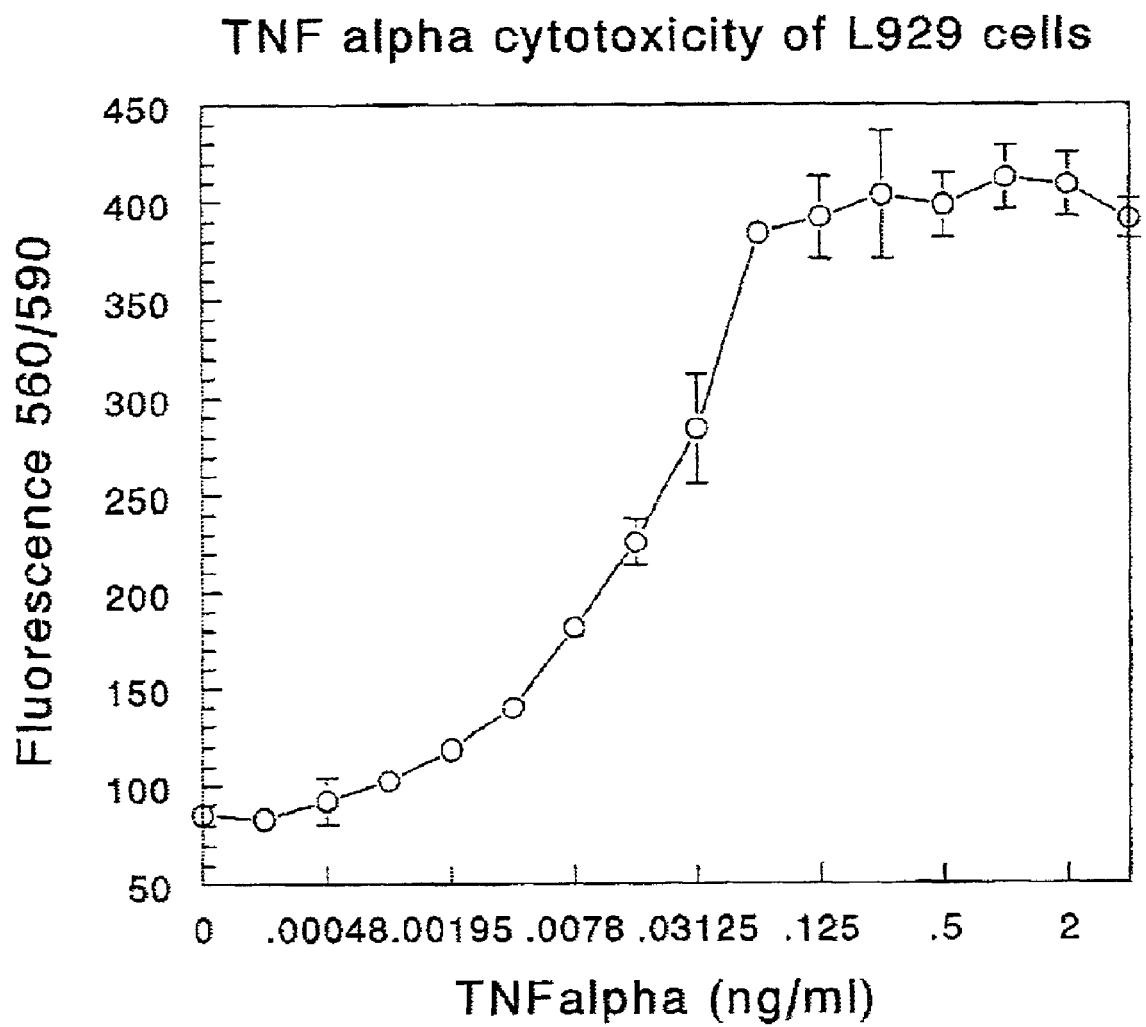
FIG. 5 is a graph depicting the cytotoxicity of TNFα as measured using the method of the present invention. TNFα concentration in ng/ml is presented on the X-axis; fluorescence is presented on the Y-axis as in FIGS. 2 through 4. See Example 3.

The results of this Example are depicted in FIG. 5. As shown in FIG. 5, the amount of observed fluorescence rose in a TNFα dose-dependent fashion at TNF concentrations ranging from zero to about 0.125 ng/ml TNF. Above about 0.125 ng/ml, the amount of observed fluorescence remained essentially constant, indicating that all of the cells in the wells had been lysed at or above this concentration of TNFα. These results indicate that the invention measures fluorescence following cell lysis at a rate proportional to lysis by a known cytotoxic agent.

What is claimed is:

1. A method for determining cytotoxicity of a test agent, the method comprising:
    (a) contacting living cells in culture medium contained in a vessel, with a pre-determined amount of the test agent; and
    (b) incubating the cells in culture medium from step (a) for a pre-determined amount of time; then
    (c) adding to the cells and culture medium from step (b) a reagent mixture that is non-toxic to the living cells, wherein the reagent mixture comprises:
        a solvent, a dye having an oxidized state and a reduced state wherein the reduced state can be distinguished from the oxidized state and wherein the dye is initially present in the oxidized state, an electron transfer agent, a substrate for a cytoplasmic enzyme having a half-life greater than two hours, and a cofactor for the cytoplasmic enzyme; and then
    (d) measuring the culture medium from step (c) for production of the reduced state of the dye, the production of the reduced state of the dye being caused by a cytoplasmic enzyme specific for the substrate in the reagent mixture added in step (c), wherein the cytoplasmic enzyme is released from dead and dying cells within the vessel, whereby the cytotoxicity of the test agent is determined.

2. The method of claim 1, wherein in step (c), the reduced state of the dye can be distinguished from the oxidized state of the dye fluorimetrically, and in step (d), the culture medium is measured for the production of the reduced state of the dye via fluorescent spectroscopy.

3. The method of claim 1, wherein in step (c), the reduced state of the dye can be distinguished from the oxidized state of the dye colorimetrically, and in step (d), the culture medium is measured for the production of the reduced state of the dye via visible spectroscopy.

4. The method of claim 1, wherein in step (c), the dye is resazurin or 3-(4,5-dimethylthiazol-2-yl)-5-(3-carboxymethoxyphenyl)-2-(4-sulphophenyl)-2H-tetrazolium, inner salt (MTS).

5. The method of claim 1, wherein in step (c), the electron transfer agent is an enzyme.

6. The method of claim 1, wherein in step (c), the electron transfer agent is diaphorase.

7. The method of claim 1, wherein in step (c), the substrate is lactate, the cofactor is NAD+, and in step (d), the production of the reduced state of the dye is caused by lactate dehydrogenase.

8. The method of claim 1, wherein in step (a), the vessel contains living cells that are prokaryotic.

9. The method of claim 1, wherein in step (a), the vessel contains living cells that are eukaryotic.

10. The method of claim 1, wherein in step (a), the vessel contains living cells that are cultured eukaryotic cells.

11. The method of claim 1, wherein in step (a), the test agent is a known or putative antibiotic.

12. The method of claim 1, wherein in step (a), the test agent is a known or putative pharmaceutical or therapeutic agent.

13. The method of claim 1, wherein: in step (b) the cells are incubated, in step (c) the reagent mixture is added, and in step (d), the culture medium is measured for production of the reduced state of the dye, all in the same vessel from step (a).

14. The method of claim 1, wherein in step (d), the culture medium is measured for production of the reduced state of the dye without separating the culture medium from the cells from step (c).

15. The method of claim 1, wherein in step (c), the solvent is an aqueous solvent.

16. The method of claim 15, wherein in step (c), the solvent is a buffered solvent.

17. The method of claim 1, A method for determining cytotoxicity of a test agent, the method comprising:
(a) contacting living cells in culture medium contained in a vessel with a pre-determined amount of the test agent: and
(b) incubating the cells in culture medium from step (a) for a pre-determined amount of time: then
(c) adding to the cells and culture medium from stem (b) a reagent mixture that is non-toxic to the living cells, wherein the reagent mixture comprises an aqueous solvent, lactate, NAD+, diaphorase, Tris buffer, HEPES, NaCl and resazurin dye; and then
(d) measuring the culture medium from step (c) for production of the reduced state of the dye, the production of the reduced state of the dye being caused by a cytoplasmic enzyme specific for the substrate in the reagent mixture added in step (c), wherein the cytoplasmic enzyme is released from dead and dying cells within the vessel, whereby the cytotoxicity of the test agent is determined.

18. The method of claim 17, wherein the reagent mixture comprises:
from about 50 mM to about 250 mM lactate;
from about 0.1 U/ml to about 10 U/ml diaphorase;
from about 0.5 mM to about 10 mM NAD+;
from about 1 mM to about 10 mM Tris buffer;
from about 10 mM to about 100 mM HEPES;
from about 1 mM to about 100 mM NaCl; and
from about 50 $\mu$M to about 500 $\mu$M resazurin.

19. The method of claim 17, wherein the reagent mixture comprises:
about 109 mM lactate;
about 3.3mM NAD+;
about 2.2 U/ml diaphorase;
about 3.0 mM Tris buffer;
about 30 mM HEPES;
about 10 mM NaCl; and
about 350 $\mu$M resazurin.

20. A method for determining cytotoxicity of a test agent, the method comprising:
(a) contacting living cells in culture medium contained in a vessel with a pre-determined amount of the test agent; and
(b) incubating the cells in culture medium from step (a) for a pre-determined amount of time; then
(c) adding to the cells and culture medium from step (b) a reagent mixture that is non-toxic to the living cells and has a pH of from about 7.0 to about 8.0., wherein the reagent mixture comprises:
a solvent, a dye having an oxidized state and a reduced state wherein the reduced state can be distinguished from the oxidized state and wherein the dye is initially present in the oxidized state, an electron transfer agent, a substrate for a cytoplasmic enzyme having a half-life greater than two hours, and a cofactor for the cytoplasmic enzyme: and then
(d) measuring the culture medium from step (c) for production of the reduced state of the dye, the production of the reduced state of the dye being caused by a cytoplasmic enzyme specific for the substrate in the reagent mixture added in step (c), wherein the cytoplasmic enzyme is released from dead and dying cells within the vessel, whereby the cytotoxicity of the test agent is determined.

21. The method of claim 20, wherein the reagent mixture has a pH of from about 7.25 to about 7.60.

22. A method for determining cytotoxicity of a test agent, the method comprising:
(a) contacting living cells in culture medium contained in a vessel with a pre-determined amount of the test agent; and
(b) incubating the cells in culture medium from step (a) for a pre-determined amount of time; then
(c) adding to the cells and culture medium from step (b) a reagent mixture that is non-toxic to the living cells, wherein the reagent mixture comprises:
a solvent, a dye having an oxidized state and a reduced state wherein the reduced state can be distinguished from the oxidized state and wherein the dye is initially present in the oxidized state, an electron transfer agent, a substrate for a cytoplasmic enzyme having a half-life treater than two hours, and a cofactor for the cytoplasmic enzyme; and then
(d) adding a stop solution to the vessel to stop any reactions taking place in the vessel; and then
(e) measuring the culture medium from step (c) for production of the reduced state of the dye, the production of the reduced state of the dye being caused by a cytoplasmic enzyme specific for the substrate in the reagent mixture added in step (c), wherein the cytoplasmic enzyme is released from dead and dying cells within the vessel, whereby the cytotoxicity of the test agent is determined.

23. The method of claim 22, wherein the stop solution comprises a soap or a detergent.

24. The method of claim 22, wherein the stop solution comprises sodium dodecylsulfate.

25. The method of claim 22, wherein the stop solution comprises sodium hydroxide.

26. A method for determining cytotoxicity of a test agent, the method comprising:
(a) contacting living cells in culture medium contained in a vessel with a pre-determined amount of the test agent; and
(b) incubating the cells in culture medium from step (a) for a pre-determined amount of time; then
(c) adding to the cells and culture medium from step (b) a reagent mixture that is non-toxic to the living cells, wherein the reagent mixture comprises:
a solvent, a dye having an oxidized state and a reduced state wherein the reduced state can be distinguished from the oxidized state and wherein the dye is initially present in the oxidized state, an electron transfer agent, a substrate for a cytoplasmic enzyme having a half-life greater than two hours, following cell lysis or cell death at 370° C. and a cofactor for the cytoplasmic enzyme; and (d) measuring the culture medium from step (c) for production of the reduced state of the dye, the production of the reduced state of the dye being caused by a cytoplasmic enzyme specific for the substrate in the reagent mixture added in step (c), wherein the cytoplasmic enzyme is released from dead and dying cells within the vessel, whereby the cytotoxicity of the test agent is determined.

27. The method of claim 26, wherein in step (c) the reagent mixture comprises a substrate for a cytoplasmic enzyme that has a half-life greater than four hours following cell lysis or cell death at 37° C.

28. The method of claim 26, wherein in step (c) the reagent mixture comprises a substrate for a cytoplasmic enzyme that has a half-life greater than six hours following cell lysis or cell death at 370° C.

29. The method of claim 26, wherein in step (c) the reagent mixture comprises a substrate for a cytoplasmic enzyme that has a half-life greater than eight hours following cell lysis or cell death at 370° C.

30. A method for determining cytotoxicity of a test agent, the method comprising:
    (a) adding a pre-determined amount of the test agent to a vessel containing living cells in culture medium; and
    (b) incubating the cells in the culture medium from step (a) for a pre-determined amount of time; then
    (c) adding a reagent mixture to the cells and culture medium from step (b) that is non-toxic to the living cells, wherein the reagent mixture comprises:
        an aqueous solvent, resazurin, an electron transfer agent, NAD+ and lactate; then
    (d) measuring the culture medium from step (c) for production of resorufin without removing the medium from the vessel, wherein the production of resorufin is caused by lactate dehydrogenase released from dead and dying cells within the vessel, whereby the cytotoxicity of the test agent is determined.

31. The method of claim 30, wherein in step (c), the electron transfer agent is diaphorase.

32. The method of claim 30, wherein in step (c), the electron transfer agent is Meldola's Blue.

33. The method of claim 30, wherein in step (a), the vessel contains living cells that are prokaryotic.

34. The method of claim 30, wherein in step (a), the vessel contains living cells that are eukaryotic.

35. The method of claim 30, wherein in step (a), the vessel contains living cells that are cultured eukaryotic cells.

36. The method of claim 30, wherein in step (a), the test agent is a known or putative toxic compound.

37. The method of claim 30, wherein in step (a), the test agent is a known or putative pharmaceutical or therapeutic agent.

38. The method of claim 30, wherein in step (d), the production of resorufin is measured fluorimetrically.

39. The method of claim 30, wherein in step (d), the production of resorufin is measured colorimetrically.

40. The method of claim 30, wherein the reagent mixture comprises an aqueous solvent, lactate, NAD+, diaphorase, Tris buffer, HEPES, NaCl and resazurin.

41. The method of claim 30, wherein the reagent mixture comprises:
    from about 50 mM to about 250 mM lactate;
    from about 0.1 U/ml to about 10 U/ml diaphorase;
    from about 0.5 mM to about 10mM NAD+;
    from about 1 mM to about 10 mM Tris buffer;
    from about 10 mM to about 100 mM HEPES;
    from about 1 mM to about 100 mM NaCl; and
    from about 50 $\mu$M to about 500 $\mu$M resazurin.

42. The method of claim 30, wherein the reagent mixture comprises:
    about 109 mM lactate;
    about 3.3 mM NAD+;
    about 2.2 U/ml diaphorase;
    about 3.0 mM Tris buffer;
    about 30 mM HEPES;
    about 10 mM NaCl; and
    about 350 $\mu$M resazurin.

43. The method of claim 30, wherein the reagent mixture has a pH of from about 7.0 to about 8.0.

44. The method of claim 30, wherein the reagent mixture has a pH of from about 7.25 to about 7.60.

45. The method of claim 30, further comprising the step of, after step (c) and prior to step (d), adding a stop solution to the vessel, to step any reactions taking place in the vessel.

46. The method of claim 45, wherein the stop solution comprises a soap or a detergent.

47. The method of claim 45, wherein the stop solution comprises sodium dodecylsulfate.

48. The method of claim 45, wherein the stop solution comprises sodium hydroxide.

* * * * *